United States Patent
Kobayashi et al.

(10) Patent No.: US 11,164,662 B2
(45) Date of Patent: Nov. 2, 2021

(54) SIMULATION METHOD, SIMULATION PROGRAM, AND SIMULATION DEVICE

(71) Applicant: SUMITOMO HEAVY INDUSTRIES, LTD., Tokyo (JP)

(72) Inventors: Yoshitaka Kobayashi, Kanagawa (JP); Daiji Ichishima, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 261 days.

(21) Appl. No.: 16/450,341

(22) Filed: Jun. 24, 2019

(65) Prior Publication Data

US 2019/0311786 A1 Oct. 10, 2019

Related U.S. Application Data

(63) Continuation of application No. PCT/JP2017/016774, filed on Apr. 27, 2017.

(51) Int. Cl.
*G16C 10/00* (2019.01)
*G16Z 99/00* (2019.01)
*G06F 30/20* (2020.01)
*G06F 111/10* (2020.01)

(52) U.S. Cl.
CPC ............. *G16C 10/00* (2019.02); *G06F 30/20* (2020.01); *G16Z 99/00* (2019.02); *G06F 2111/10* (2020.01)

(58) Field of Classification Search
CPC ......... G16C 10/00; G16C 60/00; G06F 30/20; G06F 2111/10; G16Z 99/00
See application file for complete search history.

(56) References Cited

U.S. PATENT DOCUMENTS

| | | |
|---|---|---|
| 2011/0246167 A1 | 10/2011 | Ichishima |
| 2016/0342772 A1 | 11/2016 | Ichishima |
| 2017/0017737 A1 | 1/2017 | Hirose et al. |

FOREIGN PATENT DOCUMENTS

| | | |
|---|---|---|
| JP | 2010-146368 A | 7/2010 |
| JP | 2016-218767 A | 12/2016 |
| JP | 2017-027217 A | 2/2017 |
| WO | WO-2010/070803 A2 | 6/2010 |

OTHER PUBLICATIONS

Prentis, Jeffrey J., and Daniel R. Sisan. "Granular polymer solution." Physical Review E 65.3 (2002): 031306.*
International Search Report issued in Application No. PCT/JP2017/016774, dated May 30, 2017.

* cited by examiner

*Primary Examiner* — Saif A Alhija
(74) *Attorney, Agent, or Firm* — Michael Best & Friedrich LLP

(57) ABSTRACT

A simulation method includes: a process of performing a renormalization transformation process with respect to a granular system S that is a simulation target that includes a plurality of polymers that are respectively formed of a plurality of monomer grains that are connected to each other in one dimension, on the basis of a renormalization factor $\lambda$ depending on the number of times of renormalization; and a process of calculating a position vector and a momentum vector of a monomer grain in a renormalized granular system S' by executing molecular dynamics calculation with respect to the renormalized granular system S'.

5 Claims, 6 Drawing Sheets

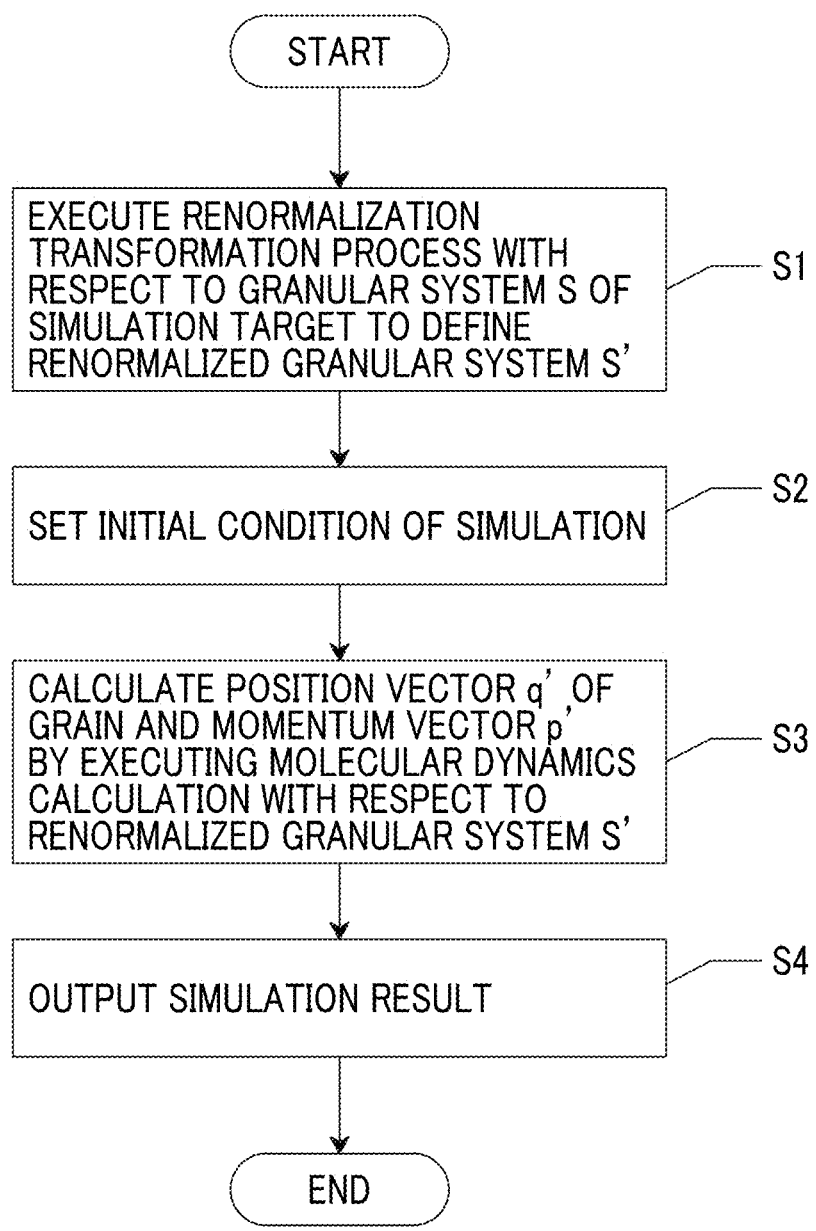

SIMULATION METHOD, SIMULATION PROGRAM, AND SIMULATION DEVICE

RELATED APPLICATIONS

The contents of International Patent Application No. PCT/JP2017/016774, on the basis of which priority benefits are claimed in an accompanying application data sheet, is in its entirety incorporated herein by reference.

BACKGROUND

Technical Field

Certain embodiments of the present invention relate to a simulation method, a simulation program, and a simulation device according to Molecular Dynamics having an application with a renormalization group.

Description of Related Art

Computer simulations using molecular dynamics are performed. In molecular dynamics, a motion equation of grains that form a system which is a simulation target is numerically solved. If the number of grains included in a system which is a simulation target increases, the amount of necessary calculation increases. The number of grains of a system capable of being simulated by a computing ability of existing computers is normally about several hundreds of thousands of pieces.

The related art discloses a simulation method using a renormalization transformation technique in order to reduce the amount of necessary calculation. Hereinafter, the renormalization transformation technique disclosed in the related art will be described.

The number of grains in a granular system S which is a simulation target is represented as N, the mass of each grain is represented as m, and an interaction potential between grains is represented as $\phi(r)$. Here, r represents an inter-grain distance. The interaction potential $\phi(r)$ is expressed as a product of an interaction coefficient $\varepsilon$ and a function $f(r)$. The interaction coefficient $\varepsilon$ represents the intensity of interaction, and has a dimension of energy. The function $f(r)$ represents dependency on an inter-grain distance, which is non-dimensional.

A first renormalization factor $\alpha$, a second renormalization factor $\gamma$, and a third renormalization factor $\delta$ are determined. The first renormalization factor $\alpha$ is larger than 1. The second renormalization factor $\gamma$ is equal to or larger than 0, and is equal to or smaller than a space dimensionality d. The third renormalization factor $\delta$ is equal to or greater than 0. When the number of renormalizations is represented as n, the first renormalization factor $\alpha$ is expressed as $\alpha = 2^n$.

The number of grains in a granular system S' which is renormalization-transformed using a renormalization technique is represented as N', the mass of each grain is represented as m', and an interaction coefficient is represented as $\varepsilon'$. The number of grains N' of the renormalization-transformed granular system S', the mass m', and the interaction coefficient $\varepsilon'$ are calculated using the following transformation equations.

$$m' = m\alpha^{\delta-\gamma}$$

$$\varepsilon' = \varepsilon\alpha^{\gamma}$$

Molecular dynamics calculation is performed with respect to the renormalization-transformed granular system S'. A position vector of each grain obtained by the molecular dynamics calculation is represented as q', and a momentum vector thereof is represented as p'. A position vector q and a momentum vector p of each grain of the granular system S may be calculated using the following equations.

$$q = q'\alpha$$

$$p = p'/\alpha^{\delta/2}$$

In a case where a granular system S is a collection of single atoms, it is possible to perform molecular dynamics calculation with respect to a renormalized granular system S' through the renormalization transformation disclosed in Japanese Patent No. 524168. As a method for performing the molecular dynamics calculation with respect to the granular system S configured of multiple polymer molecules, the Kremer-Grest model has been proposed. A method for performing simulations by applying the renormalization transformation process to the Kremer-Grest model is not established.

SUMMARY

According to an embodiment of the present invention, there is provided a simulation method including:

a process of performing a renormalization transformation process with respect to a granular system S that is a simulation target that includes a plurality of polymers that are respectively formed of a plurality of monomer grains that are connected to each other in one dimension, on the basis of a renormalization factor $\lambda$ depending on the number of times of renormalization; and a process of calculating a position vector and a momentum vector of a monomer grain in a renormalized granular system S' by executing molecular dynamics calculation with respect to the renormalized granular system S', in which when a distance between monomers in the granular system S and the granular system S' is represented as r, a dimensionality of a space is represented as d, a mass of a monomer in the granular system S is represented as m, the number of monomer grains that form one polymer is represented as Nm, the number of polymers is represented as Np, and a coordinate of the monomer grain is represented as q, as an interaction potential $\phi(r)$ between the monomer grains, the following equation is applied in unspecified monomer grains, $$\phi(r) = U_0(r)$$

where a potential $U_0(r)$ is expressed as follows, using a parameter $\varepsilon$ having a dimension of energy, a parameter $\sigma$ having a dimension of a length, and a non-dimensional function f, $$U_0(r) = \varepsilon f\left(\frac{r}{\sigma}\right)$$

the following equation obtained by adding a finite extension non-linear elastic potential $U_{ch}(r: \varepsilon, \sigma)$ having the parameters $\varepsilon$ and $\sigma$ used in the potential $U_0(r)$ as parameters to the potential $U_0(r)$ is applied in the monomer grains that are adjacent to each other in the same polymer, $$\phi(r) = U_0(r) + U_{ch}(r:\varepsilon,\sigma)$$

when a mass of a monomer grain in the granular system S' is represented as m', the number of monomer grains that form one polymer is represented as Nm', the number of polymers is represented as Np', and a coordinate of the monomer grain is represented as q', the following transformation law is applied, and $$q' = q$$
$$m' = m\lambda^d$$
$$N'_m = \frac{N_m}{\lambda}$$
$$N'_p = \frac{N_p}{\lambda^{d-1}}$$
$$\varepsilon' = \varepsilon\lambda^{de}$$
$$\sigma' = \sigma\lambda$$

the molecular dynamics calculation is executed with respect to the granular system S' using potentials $U_0'(r)$ and $U_{ch}'(r: \varepsilon, \sigma)$ in the granular system S' corresponding to the potentials $U_0(r)$ and $U_{ch}(r: \varepsilon, \sigma)$ in the granular system S expressed as follows:

$$U_0'(r) = \varepsilon' f\left(\frac{r}{\sigma'}\right)$$
$$U_{ch}'(\varepsilon, \sigma, r) = U_{ch}(r:\varepsilon', \sigma')$$

BRIEF DESCRIPTION OF THE DRAWINGS

FIG. 1 is a flowchart of a simulation method according to an embodiment.

FIG. 2 is a schematic diagram showing a state where a grain i, a grain j, and a grain k are sequentially arranged in one dimension.

DETAILED DESCRIPTION

Figure 3:
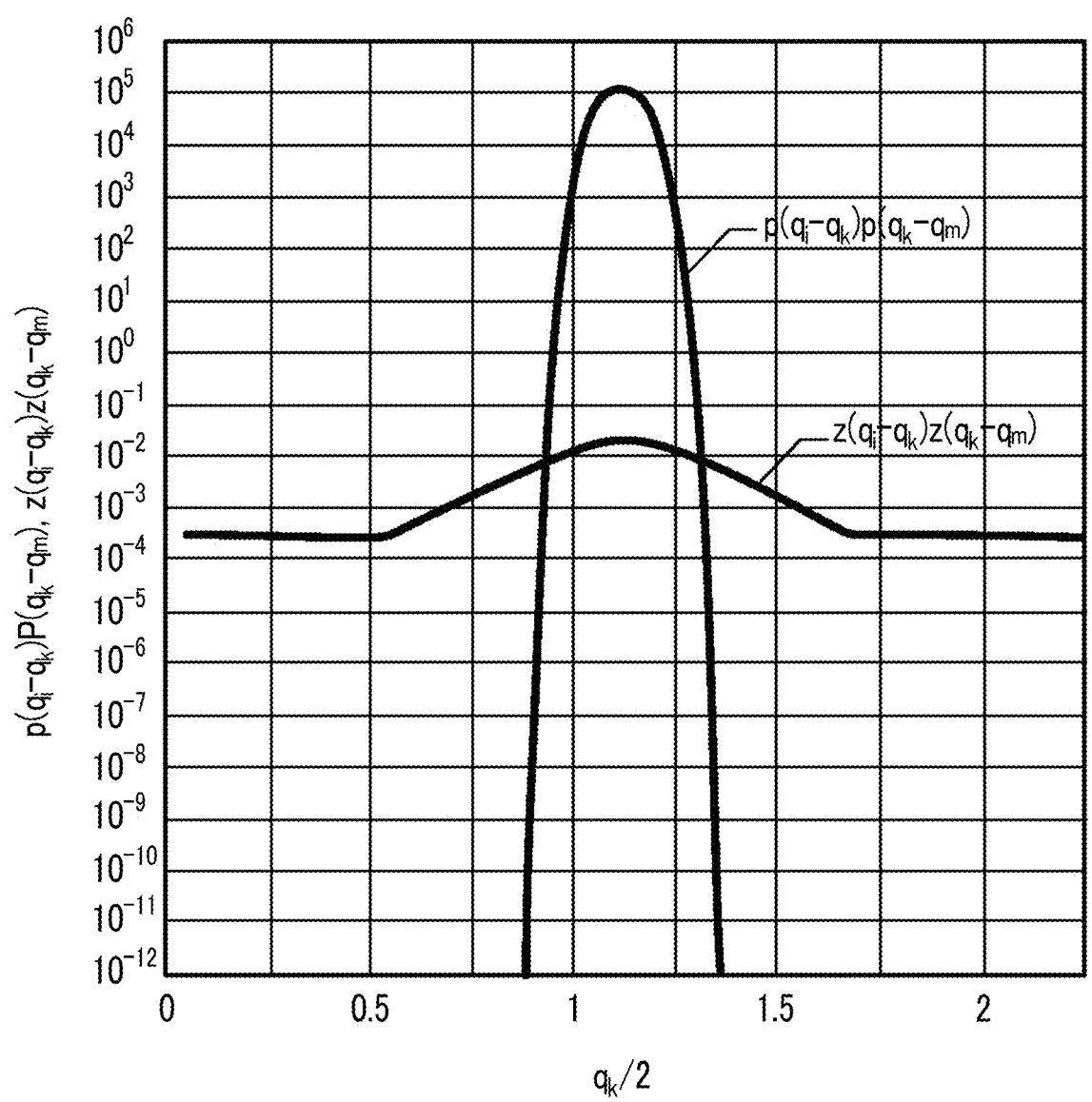
FIG. 3 is a graph showing a calculation result of Equation (27) and a numerical integration result of Equation (28) in a case where an interaction potential φ(r) is a Lennard-Jones potential.

It is desirable to provide a method for simulating behaviors of monomer molecules by applying a way of thinking of a renormalization group to a granular system formed by polymer molecules. Further, it is desirable to provide a computer program for performing the simulation method. Furthermore, it is desirable to provide a simulation device that executes the simulation method.

According to another embodiment of the invention, there are provided a computer program for executing the simulation, a recording medium on which the computer program is recorded, and a simulation device.

By applying renormalization transformation to a granular system formed by polymers in which a plurality of monomer grains are connected to each other in a chain shape, it is possible to perform molecular dynamics calculation. Thus, it is possible to reduce a calculation time.

Molecular Dynamics applied to an embodiment of the invention will be briefly described. A granular system formed of N grains (for example, atoms) and having a Hamiltonian H expressed as the following equation will be described.

$$H = \sum_{j=1}^{N} \left[ \frac{\vec{p}_j^2}{2m} + \sum_{i=j+1}^{N} \phi(|\vec{q}_i - \vec{q}_j|) \right] \quad (6)$$

Here, m represents the mass of a grain, φ represents an interaction potential between grains, a vector $p_j$ represents a momentum vector of the grain, and a vector $q_j$ represents a position vector (position coordinates) of the grain.

By substituting the Hamiltonian H in a Hamiltonian canonical equation, the following motion equation with respect to a grain j is obtained.

$$\frac{d\vec{p}_j}{dt} = -\sum_{i=j}^{N-1} \left[ \frac{\partial \phi(|\vec{q}_i - \vec{q}_j|)}{\partial \vec{q}_j} \right] \quad (7)$$

$$\frac{d\vec{q}_j}{dt} = \frac{\vec{p}_j}{m} \quad (8)$$

In molecular dynamics, by solving the motion equations expressed by Equation (7) and Equation (8) by numerical integration with respect to each grain that forms a granular system, the momentum vector $p_j$ and the position vector $q_j$ of each grain at each time point are obtained. In many cases, a Verlet algorithm is used in the numerical integration. The Verlet algorithm is described in page 175 of "Computational Physics", J. M. Thijssen (Cambridge University Press 1999), for example. Various physical quantities of a granular system may be calculated based on a momentum vector and a position vector of each grain obtained through molecular dynamics calculation.

Next, molecular dynamics using a renormalization group technique (hereinafter, referred to as renormalization group molecular dynamics) will be conceptually described.

In the renormalization group molecular dynamics, a granular system S which is a simulation target is associated with a granular system S' (hereinafter, referred to as a renormalized granular system S') formed of grains smaller in number than grains in the granular system S. Then, the molecular dynamics calculation is executed with respect to the renormalized granular system S'. A calculation result with respect to the renormalized granular system S' is associated with the granular system S which is the simulation target. Thus, it is possible to reduce the amount of calculation, compared with a case where the molecular dynamics calculation is directly executed with respect to the granular system S which is the simulation target. A transformation law for associating physical quantities (for example, the number of grains, the mass of a grain, and the like) in the granular system S which is the simulation target with the physical quantity in the renormalized granular system S' is referred to as a renormalization transformation law.

FIG. 1 shows a flowchart of a simulation method according to an embodiment. In step S1, a renormalization transformation process is executed based on the renormalization transformation law with respect to the granular system S which is the simulation target to define the renormalized granular system S'. The granular system S is configured of a plurality of polymers, in which each of the plurality of polymers is configured of a plurality of polymer grains that are connected to each other in one dimension.

As an interaction potential $\phi(r)$ between monomer grains in the granular system S, Equation (9) is applied between unspecified monomer grains.

$$\phi(r)=U_0(r) \tag{9}$$

Here, r represents a distance between respective grains that form the granular system S.

A potential $U_0(r)$ is basically expressed as the following equation.

$$U_0(r) = \varepsilon f\left(\frac{r}{\sigma}\right) \tag{10}$$

Here, f represents a non-dimensional function, and $\varepsilon$ and $\sigma$ represent parameters characterizing a monomer grain. The parameter $\varepsilon$ has a dimension of energy, and is called as an interaction coefficient. The parameter $\sigma$ has a dimension of a distance, and depends on the size of the grain.

Between monomer grains that are adjacent to each other in the same polymer, a finite extension non-linear elastic potential $U_{ch}(r: \varepsilon, \sigma)$ is added to the potential $U_0(r)$, so that Equation (11) is applied.

$$\phi(r)=U_0(r)+U_{ch}(r:\varepsilon,\sigma) \tag{11}$$

The finite extension non-linear elastic potential $U_{ch}(r: \varepsilon, \sigma)$ includes parameters that depend on the parameters $\varepsilon$ and $\sigma$ for defining the potential $U_0(r)$.

As the potential $U_0(r)$, for example, a Lennard-Jones potential may be applied. In a case where a shifted Lennard-Jones potential is applied to the potential $U_0(r)$, the potential $U_0(r)$ may be defined as the following equation, for example.

$$U_0(r) = 4\varepsilon\left[\left(\frac{\sigma}{r}\right)^{12} - \left(\frac{\sigma}{r}\right)^{6} + \frac{1}{4}\right] \left(r \le 2^{\frac{1}{6}}\sigma\right) \tag{12}$$

$$U_0(r) = 0 \quad \left(r > 2^{\frac{1}{6}}\sigma\right)$$

As the potential $U_0(r)$, a Morse potential may also be applied. Further, an approximate function obtained by Taylor-expanding the functions may also be used as the potential $U_0(r)$. In this embodiment, an example in which the Lennard-Jones potential is applied as the potential $U_0(r)$ will be described.

A position vector q of a monomer grain of the granular system S which is a simulation target, a mass m of the monomer grain, the number of monomer grains Nm in a polymer, the number of polymers Np, and the parameters $\varepsilon$ and $\sigma$ that define the potential $U_0(r)$ are respectively transformed into a position vector q' of a granular system S' which is a simulation target, a mass m' of the monomer grain, the number of monomer grains Nm' in a polymer, the number of polymers Np', and the parameters $\varepsilon$' and $\sigma$' that define a potential $U_0'(r)$, through a renormalization transformation process. In the renormalization transformation process in step S1, the renormalization transformation law is applied.

$$q' = q \tag{13}$$
$$m' = m\lambda^d$$
$$N_m' = \frac{N_m}{\lambda}$$
$$N_p' = \frac{N_p}{\lambda^{d-1}}$$
$$\varepsilon' = \varepsilon\lambda^d$$
$$\sigma' = \sigma\lambda$$

Here, d represents a dimensionality of a space where the granular system S which is the simulation target is arranged. $\lambda$ represents a renormalization factor depending on the number of times of renormalization. When the number of times of renormalization is n, the renormalization factor $\lambda$ is expressed as the following equation.

$$\lambda=2^n \tag{14}$$

As the potential $U_0'(r)$ and a potential $U_{ch}'(r: \varepsilon, \sigma)$ in the granular system S' corresponding to the potential $U_0(r)$ and a potential $U_{ch}(r: \varepsilon, \sigma)$ in the granular system S, the following potentials are used.

$$U_0'(r) = \varepsilon' f\left(\frac{r}{\sigma'}\right) \tag{15}$$

$$U_{ch}'(r:\varepsilon, \sigma) = U_{ch}(r:\varepsilon', \sigma')$$

An interaction potential $\phi'(r)$ applied between unspecified monomer grains in the granular system S' is defined by the following equation.

$$\phi'(r)=U_0'(r) \tag{16}$$

Between monomer grains that are adjacent to each other in the same polymer, the finite extension non-linear elastic potential $U_{ch}'(r: \varepsilon, \sigma)$ is added to the potential $U_0'(r)$, and Equation (17) is applied as the interaction potential $\phi'$.

$$\phi'(r)=U_0'(r)+U_{ch}'(r:\varepsilon',\sigma') \tag{17}$$

By applying the above-described renormalization transformation law, the number of grains becomes $1/\lambda^d$ times, and the mass of a grain becomes $\lambda^d$ times. Thus, the entire mass of the granular system S and the entire mass of the granular system S' are the same. Further, since the position vector q' of the monomer grain in the granular system S' and the position vector q of the monomer grain in the granular system S are the same, macroscopic dimensions between the granular system S and the renormalized granular system S' are the same. Since the entire mass of the granular system and the dimension thereof do not change before and after the renormalization transformation process, the density of the granular system is not also changed.

Then, in step S2, initial conditions of a simulation are set. The initial conditions include initial values of the position vector $q_j$ and the momentum vector $p_j$ of each grain. The momentum vector $p_j$ is set based on a temperature T' of the renormalized granular system S'. When the temperature of the granular system S which is the simulation target is represented as T, the following renormalization transformation law is applied with respect to the temperature.

$$T' = T\lambda^d \quad (18)$$

Then, in step S3, molecular dynamics calculation is executed with respect to the renormalized granular system S'. Its motion equation is expressed as the following equation.

$$\frac{d\vec{p}'_j}{dt'} = -\sum_{i \neq j}^{N'} \left[ \frac{\partial \phi'(|\vec{q}'_i - \vec{q}'_j|)}{\partial \vec{q}'_j} \right] \quad (19)$$

$$\frac{d\vec{q}'_i}{dt'} = \frac{\vec{p}'_i}{m'}$$

Here, N' represents a total number of monomer grains in the granular system S', and N'=Nm'×Np'.

The motion equation is solved by numerical integration. Thus, time histories of a position vector q' and a momentum vector p' of each grain of the renormalized granular system S' are calculated.

A correspondence between the position vector q' of each grain in the renormalized granular system S' and the position vector q of each grain in the granular system S which is the simulation target is as shown in Equation (13). The momentum vector p' in the renormalized granular system S' and the momentum vector p in the granular system S which is the simulation target have the following relationship.

$$\vec{p}' = \lambda^d \vec{p} \quad (20)$$

In step S4, the simulation result is output. For example, the position vector q' and the momentum vector p' may be output as numerical values as they are, or may be displayed as an image obtained by imaging a distribution of plural grains in the granular system S' in a space based on the position vector q'.

[Consideration with Respect to a Case where $\phi(r)$ is $U_0(r)$]

Next, the renormalization transformation law is derived with respect to a case where the interaction potential $\phi(r) = U_0(r)$. First, the Hamiltonian H' of the renormalized granular system S' is expressed as Equation (21).

$$H' = \sum_{j=1}^{N'} \left[ \frac{\vec{p}'^2_j}{2m'} + \sum_{i=j+1}^{N'} \varepsilon' f\left(\frac{|\vec{q}'_i - \vec{q}'_j|}{\sigma'}\right) \right] \quad (21)$$

The number of grains in the granular system S before renormalization is represented as N, and the number of grains of the renormalized granular system S' is expressed as N'. By substituting the Hamiltonian H' in a canonical equation, it is possible to obtain a motion equation. The renormalization transformation law of Equation (13) is derived from parameters of the Hamiltonian H'.

In order to obtain the Hamiltonian H' of the renormalized granular system S', a part of integration of a partition function $Z(\beta)$ with respect to the granular system S may be executed to perform coarse graining with respect to a Hamiltonian, to thereby obtain the Hamiltonian H'.

The partition function $Z(\beta)$ with respect to a canonical ensemble having a constant number of grains is expressed as the following equation.

$$Z(\beta) = \int d\Gamma_N \exp(-\beta H(p, q)) \quad (22)$$

$$\beta \equiv \frac{1}{k_B T}$$

Here, $k_B$ represents a Boltzmann's constant, and $d\Gamma_N$ represents a volume element in a phase space. $d\Gamma_N$ is expressed as the following equation.

$$d\Gamma_N = \frac{1}{W_N} \prod_{j=1}^{N} d\vec{p}_i \cdot d\vec{q}_i \equiv \frac{1}{W_N} D_p^N D_q^N \quad (23)$$

$$D_p^N \equiv \prod_{j=1}^{N} d\vec{p}_i$$

$$D_q^N \equiv \prod_{j=1}^{N} d\vec{q}_i$$

$$W_N = N! \cdot h^{3N}$$

Here, h represents a Planck constant. $W_N$ is determined so that an intrinsic quantal sum of all states and integration over the phase space match each other.

First, coarse graining of an interaction potential between grains will be described, and then, coarse graining of a kinetic energy will be described. Subsequently, the renormalization transformation law is defined based on the coarse graining of the interaction potential and the coarse graining of the kinetic energy.

[Coarse Graining of Interaction Potential $\phi = U_0$ Between Monomer Grains]

First, coarse graining of an interaction potential in a granular system where grains are arranged in a one-dimensional chain pattern will be described. Then, an interaction potential in grains which are arranged in a simple cubic lattice pattern will be described.

As shown in FIG. 2, a grain i, a grain j, and a grain k are sequentially arranged in a one-dimensional pattern. By writing an interaction relating to the grain j and executing integration with respect to position coordinates of the grain j positioned in the middle of the grain i and the grain k, it is possible to perform coarse graining of the interaction potential. First, in order to reflect contribution from a next-nearest or more distant grain, a potential moving method may be used. The potential moving method is described in "STATISTICAL PHYSICS Static, Dynamics and Renormalization", Chap. 14, World Scientific (1999) by Leo P. Kadanoff.

An interaction potential $\phi$ Tilda in which the contribution from the next-nearest or more distant grain is reflected may be expressed as the following equation.

$$\tilde{\phi}(r) = \phi(r) + \phi(r+a) + \phi(r+2a) + \ldots \quad (24)$$

Here, a represents an inter-grain distance in an equilibrium state. The inter-grain distance a in the equilibrium state may be equivalent to a distance where the interaction potential $\phi(r)$ becomes minimum.

Since plural grains are arranged in one dimension, the position vector $q_j$ of the grain j may be expressed as a one-dimensional coordinate $q_j$. If the position of the grain j is expressed as $q_j$, a cage potential made by a nearest grain with respect to the grain j is expressed as the following equation.

$$\tilde{\phi}(q_i - q_j) + \tilde{\phi}(q_j - q_k) = \tilde{\phi}\left(\frac{q_i - q_k}{2} + \frac{q_i + q_k - 2q_j}{2}\right) + \quad (25)$$
$$\tilde{\phi}\left(\frac{q_i - q_k}{2} - \frac{q_i + q_k - 2q_j}{2}\right)$$
$$= \tilde{\phi}\left(\frac{q_i - q_k}{2} + x_j\right) + \tilde{\phi}\left(\frac{q_i - q_k}{2} - x_j\right)$$
$$= 2\left[\tilde{\phi}\left(\frac{q_i - q_k}{2}\right) + \sum_{n=1}^{\infty} \frac{1}{2n!}\tilde{\phi}^{(2n)}\left(\frac{q_i - q_k}{2}\right)x_j^{2n}\right]$$

$$x_j \equiv \frac{q_i + q_k - 2q_j}{2}$$

If integration is executed with respect to $q_j$ which is an integration variable, the following equation is obtained using Equation (25).

$$\frac{\int_{q_i+r_a}^{q_k-r_a} dq_j \exp[-\beta\{\tilde{\phi}(q_i-q_j)+\tilde{\phi}(q_j-q_k)\}]}{P(q_i-q_k)} = z(q_i-q_k) \quad (26)$$

Here, $r_a$ represents the diameter of a grain, and $z(q_i-q_k)$ and $P(q_i-q_k)$ are expressed as the following equations.

$$P(q_i - q_k) = \exp\left[-2\beta\tilde{\phi}\left(\frac{q_i - q_k}{2}\right)\right] \quad (27)$$

$$z(q_i - q_k) = \int_{q_i-r_a}^{r_a-q_k} dx_j \exp\left[-2\beta\sum_{n=1}^{\infty}\frac{1}{2n!}\tilde{\phi}^{(2n)}\left(\frac{q_i - q_k}{2}\right)x_j^{2n}\right] \quad (28)$$

An integration region is limited to an inner region of the cage potential.

Then, $z(q_i-q_k)$ is specifically calculated. In a case where the interaction potential $\phi$ is the Lennard-Jones potential, $\phi^{(2n)}$ is expressed as the following equation.

$$\phi^{(2n)}(r) = \frac{4\varepsilon}{\sigma^{2n}}\left[\frac{(2n+11)!}{11!}\left(\frac{\sigma}{r}\right)^{2n+12} - \frac{(2n+5)!}{5!}\left(\frac{\sigma}{r}\right)^{2n+6}\right] \quad (29)$$

Numerical integration is performed by substituting Equation (29) in Equation (28). In substituting Equation (29) in Equation (28), Equation (24) is used.

FIG. 3 shows a calculation result of Equation (27) and a numerical integration result of Equation (28) in a case where the interaction potential $\phi(r)$ is the Lennard-Jones potential. In a case where a grain i, a grain j, a grain k, a grain l, and a grain m are sequentially arranged in one dimension, a position coordinate of the grain k is expressed as $q_k$. A transverse axis in FIG. 3 represents $q_k/2$, and a longitudinal axis represents $P(q_i-q_k)P(q_k-q_m)$ and $z(q_i-q_k)z(q_k-q_m)$ in a logarithmic scale. In the numerical value calculation in FIG. 3, $\varepsilon/k_BT=2.0$.

From FIG. 3, it can be understood that a change in $z(q_i-q_k)z(q_k-q_m)$ is smoother than a change in $P(q_i-q_k)P(q_k-q_m)$. Thus, $z(q_i-q_k)z(q_k-q_m)$ may be nearly approximated as a constant with respect to $P(q_i-q_k)P(q_k-q_m)$.

A probability $p(q_k)$ that the grain k is present in the position coordinate $q_k$ may be approximated as follows.

$$p(q_k) = \frac{z(q_i - q_k)z(q_k - q_m)P(q_i - q_k)P(q_k - q_m)}{\int_{q_i+r_a}^{q_m-r_a} dq_k z(q_i - q_k)z(q_k - q_m)P(q_i - q_k)P(q_k - q_m)} \quad (30)$$
$$\cong \frac{P(q_i - q_k)P(q_k - q_m)}{\int_{q_i+r_a}^{q_m-r_a} dq_k P(q_i - q_k)P(q_k - q_m)}$$

Accordingly, the following equation is derived.

$$\int_{q_i+r_a}^{q_k-r_a} dq_j \exp[-\beta\{\tilde{\phi}(q_i-q_j)+\tilde{\phi}(q_j-q_k)\}] \propto \exp\left[-2\beta\tilde{\phi}\left(\frac{q_i-q_k}{2}\right)\right] \quad (31)$$

Hereinbefore, coarse graining of an interaction potential of a granular system in which plural grains are arranged in one dimension is described. An interaction potential of a multi-dimensional granular system may be realized by a potential moving method.

A potential moving method for returning a two-dimensional lattice to a one-dimensional lattice will be described with reference to FIGS. 4A to 4C.

Figure 4A:
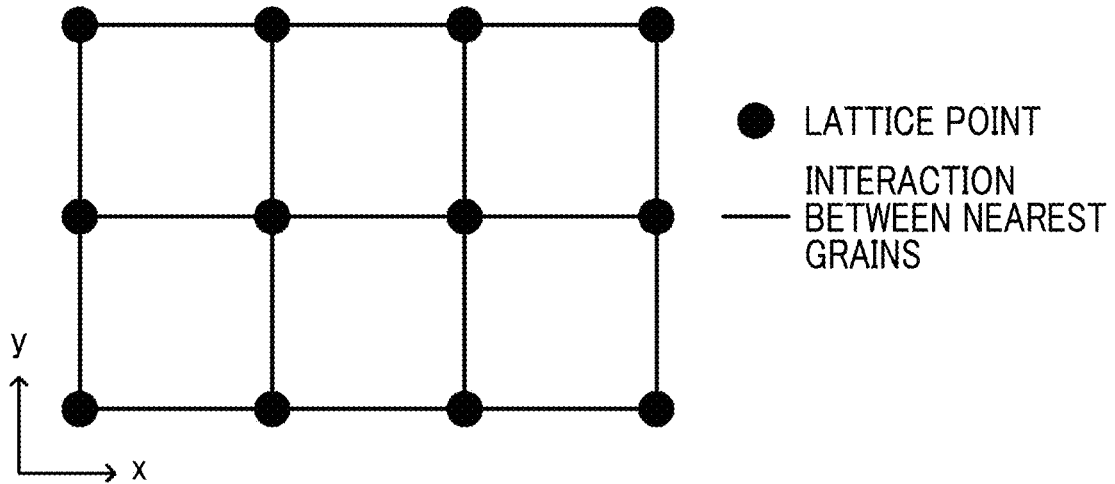
FIGS. 4A to 4C are diagrams for describing a potential moving method for returning a two-dimensional lattice to a one-dimensional lattice.

As shown in FIG. 4A, grains are arranged at positions of lattice points of a two-dimensional square lattice. An interaction between nearest grains (nearest-neighbor-coupling) is indicated by a solid line. One direction where grains are arranged is defined as an x direction, and a direction orthogonal thereto is defined as a y direction.

Figure 4B:
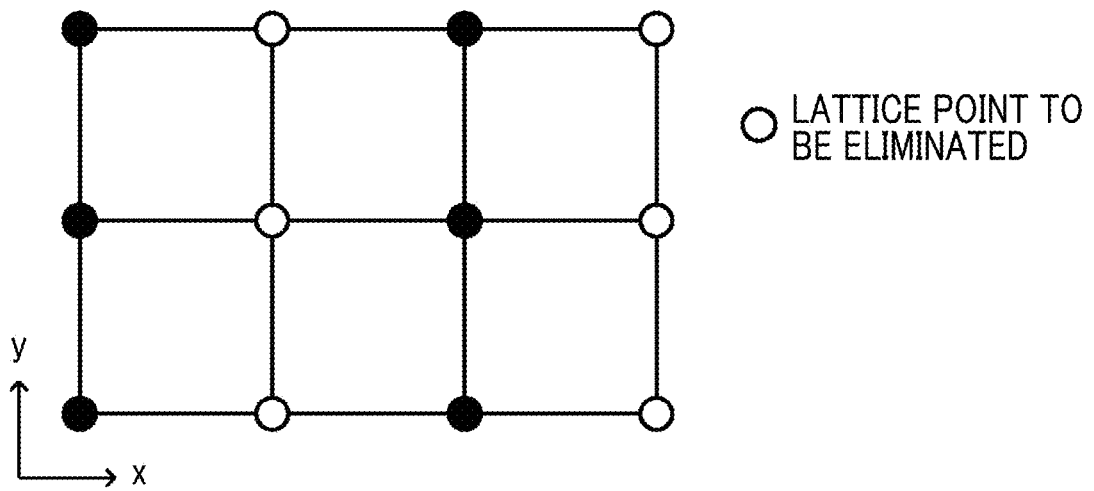

As shown in FIG. 4B, it is considered that integration is executed with respect to displacements of grains (grains indicated by hollow circles) which are alternately arranged among grains arranged in the x direction. A grain which is an integration target (a grain to be eliminated) is referred to as an integration target grain.

Figure 4C:
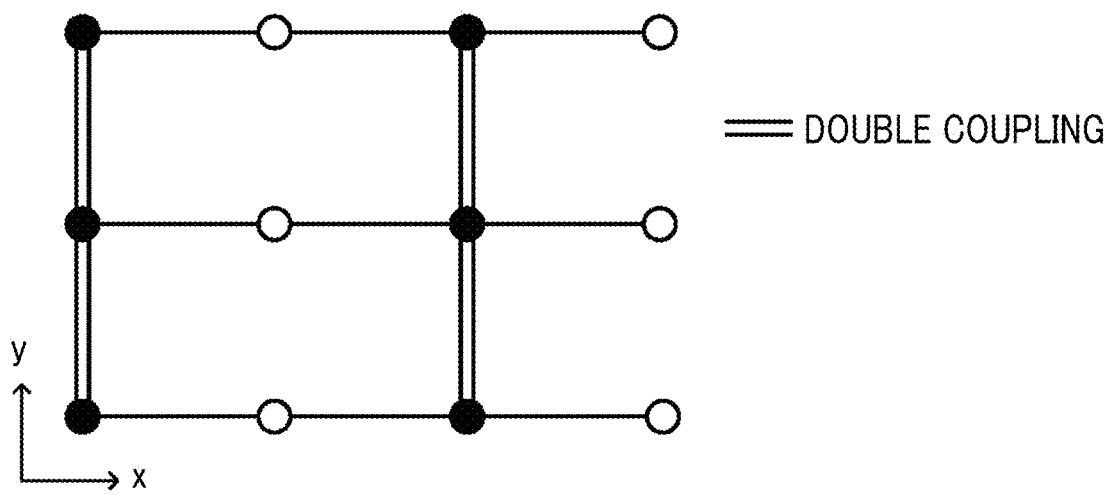

As shown in FIG. 4C, in the potential moving method, the nearest-neighbor-coupling of integration target grains is divided into grains which are adjacently arranged in the x direction. A grain interaction (double coupling) obtained by adding up divided interactions is indicated by a double-line. The double coupling indicated by the double-line has a strength two times the original nearest-neighbor-coupling. Using such a method, it is possible to transform a two-dimensional lattice into a one-dimensional chain. In the granular system of the one-dimensional chain, it is possible to perform coarse graining of an interaction potential by the method described with reference to FIG. 2. In a case where a granular system which is a simulation target forms a three-dimensional lattice, a procedure of transforming a two-dimensional lattice into a one-dimensional chain may be repeated in three directions of the x direction, the y direction, and the z direction. In this way, it is possible to perform coarse graining of a granular system that forms a multi-dimensional lattice.

Coarse graining of an interaction potential of a granular system that forms a multi-dimensional (dimensionality d) lattice is expressed as the following equation.

$$\int D_q^N \exp\left(-\beta \sum_{j=1}^{N} \sum_{i=j+1}^{N} \phi(|\bar{q}_i - \bar{q}_j|)\right) \propto \quad (32)$$

$$\int D_q^{N'} \exp\left(-\beta \sum_{<i,j>} 2^d \tilde{\phi}\left(\frac{|\bar{q}_i - \bar{q}_j|}{2}\right)\right)$$

$$N' = \frac{N}{2^d}$$

Here, $<i, j>$ means that a sum is taken between nearest lattices.

If the sum between the nearest lattices is changed with respect to the sum of all interactions, the following equation is obtained.

$$\int D_q^N \exp\left(-\beta \sum_{j=1}^{N} \sum_{i=j+1}^{N} \phi(|\vec{q}_i - \vec{q}_j|)\right) \propto \qquad (33)$$

$$\int D_q^{N'} \exp\left(-\beta \sum_{j=1}^{N'} \sum_{i=j+1}^{N'} 2^d \tilde{\phi}\left(\frac{|\vec{q}_i - \vec{q}_j|}{2}\right)\right)$$

[Coarse Graining of Kinetic Energy]

Next, coarse graining of a kinetic energy will be described. Integration may be easily executed with respect to the kinetic energy, and accordingly, the following equation is derived.

$$\int D_p^N \exp\left(-\beta \sum_{j=1}^{N'} \frac{\vec{p}_j^2}{2m}\right) \propto \int D_p^{N'} \exp\left(-\beta \sum_{j=1}^{N'} \frac{\vec{p}_j^2}{2m}\right) \qquad (34)$$

In derivation of Equation (34), the following equation is used. Here, a momentum vector $p_j^2$ means an inner product of the vector.

$$\int \cdots \int d\vec{p}_i d\vec{p}_j d\vec{p}_k \cdots \exp\left(\cdots -\beta \frac{\vec{p}_i^2}{2m} - \beta \frac{\vec{p}_j^2}{2m} - \beta \frac{\vec{p}_k^2}{2m} \cdots\right) = \qquad (35)$$

$$\sqrt{\frac{2m}{\beta}} \int \cdots \int d\vec{p}_i d\vec{p}_k \cdots \exp\left(\cdots -\beta \frac{\vec{p}_i^2}{2m} - \beta \frac{\vec{p}_k^2}{2m} \cdots\right)$$

[Derivation of Renormalization Transformation Law]

Next, a renormalization transformation law derived from coarse graining of the above-described interaction potential and coarse graining of a kinetic energy will be described.

By substituting Equation (33) and Equation (34) in Equation (22) to eliminate coefficients which do not affect a result, the following equation is obtained.

$$Z(\beta) = \int d\Gamma_{N'} \exp\left[-\beta \sum_{j=1}^{N'} \left\{\frac{\vec{p}_j^2}{2m} + \sum_{i=j+1}^{N'} 2^d \varepsilon f\left(\frac{|\vec{q}_i - \vec{q}_j|}{2\sigma}\right)\right\}\right] \qquad (36)$$

From Equation (36), a Hamiltonian H' (Hamiltonian of the renormalized granular system S') which is subjected to coarse graining is expressed as the following equation.

$$H' = \sum_{j=1}^{N'} \left\{\frac{\vec{p}_j^2}{2m} + \sum_{i=j+1}^{N'} 2^d \varepsilon f\left(\frac{|\vec{q}_i - \vec{q}_j|}{2\sigma}\right)\right\} \qquad (37)$$

$$N' = \frac{N}{2^d}$$

A list of coupling constants when performing coarse graining of the Hamiltonian is represented as K. The list K of the coupling constants is expressed as follows.

$$K = (m, \varepsilon, \sigma) \qquad (38)$$

The renormalization transformation R is defined as follows.

$$K' = R(K) = (2^d m, 2^d \varepsilon, 2\sigma) \qquad (39)$$

A list $K_n$ of coupling coefficients after renormalization transformation is executed n times is expressed as the following equation.

$$K_n = R \circ \ldots \circ R(K) = (\lambda^d m, \lambda^d \varepsilon, \lambda \sigma) \qquad (40)$$

Accordingly, a Hamiltonian Hn after renormalization transformation is performed n times is expressed as the following equation.

$$H_n = R \circ \cdots \circ RH \qquad (41)$$

$$= \sum_{j=1}^{\frac{N}{\lambda^d}} \left\{\frac{\vec{p}_j'^2}{2\lambda^d m} + \sum_{i=j+1}^{\frac{N}{\lambda^d}} \lambda^d \varepsilon f\left(\frac{|\vec{q}_i - \vec{q}_j|}{\sigma \lambda}\right)\right\}$$

Here, the momentum vector $p_j'$ in the renormalized granular system S' is expressed as the following equation.

$$\vec{p}_j' = \lambda^d \vec{p}_j \qquad (42)$$

The renormalization transformation law shown in Equation (13) is derived from Equation (21) and Equation (41)

[Consideration with Respect to a Case where Interaction Potential $\phi$ Between Monomer Grains is $U_0 + U_{ch}$]

Next, the derivation of the renormalization transformation law relating to the interaction potential $\phi(r)$ between monomer grains which are adjacent to each other in a polymer will be described.

In FIG. 2, a cage potential with respect to the grain j, formed by the grains i and k, may be expressed as the following Equation, in a similar way to Equation (25).

$$\phi(q_i - q_j) + \phi(q_j - q_k) = 2\left[\phi\left(\frac{q_i - q_k}{2}\right) + \sum_{n=1}^{\infty} \frac{1}{2n!} \phi^{(2n)}\left(\frac{q_i - q_k}{2}\right) x_j^{2n}\right] \qquad (43)$$

$$x_j \equiv \frac{q_i + q_k - 2q_j}{2}$$

With respect to the integration variable $q_j$, integration is performed from a position where the monomer grain j is in contact with one monomer grain i to a position where the monomer grain j is in contact with the other monomer grain k. When the diameter of the monomer grain is represented as $r_a$, the following equation is obtained.

$$\int_{q_i + r_a}^{q_k - r_a} dq_j \exp[n\beta\{\phi(q_i - q_j) + \phi(q_j - q_k)\}] = \qquad (44)$$

$$\exp\left[-2\beta\phi\left(\frac{q_i - q_k}{2}\right) - \beta\delta\phi\right]$$

$$\delta\phi = -\beta^{-1} \log\left[\int_{q_k + r_a}^{q_k - r_a} dx_j \exp\left\{-2\beta \sum_{n=0}^{\infty} \frac{1}{2n!} \phi^{(2n)}\left(\frac{q_i - q_k}{2}\right) x_j^{2n}\right\}\right]$$

As shown in the equation, the interaction potential after the renormalization becomes an overlay of functions of $2\phi((q_i - q_k)/2)$ and $\delta\phi$.

As the finite extension non-linear elastic potential $U_{ch}(r: \varepsilon, \sigma)$, the following potential that is known as the Kremer-Grest model may be employed.

$$U_{ch}(r:\varepsilon, \sigma) = -\frac{1}{2}kR_0^2 \ln\left[1 - \left(\frac{r}{R_0}\right)^2\right] \quad (r \leq R_0) \quad (45)$$

$$U_{ch}(r:\varepsilon, \sigma) = \infty \quad (r > R_0)$$

Here, parameters k and $R_0$ are determined depending on the parameters $\varepsilon$ and $\sigma$ that are shown in Equation (10). For example, the parameters k and $R_0$ are defined by the following equation.

$$k = \frac{30\varepsilon}{\sigma^2} \quad (46)$$

$$R_0 = 1.5\sigma$$

In a case where the relationship of Equation (46) is applied, the finite extension non-linear elastic potential $U_{ch}(r: \varepsilon, \sigma)$ may be expressed as the following equation, in a similar way to the potential $U_0(r)$ shown in Equation (10). Here, $f_{ch}$ represents a non-dimensional function.

$$U_{ch}(r:\varepsilon, \sigma) = \varepsilon f_{ch}\left(\frac{r}{\sigma}\right) \quad (47)$$

The interaction potential $\phi(r)$ is expressed as the following equation.

$$\phi(r) = U_0(r) + U_{ch}(r:\varepsilon, \sigma) \quad (48)$$

The potential $U_0(r)$ is as shown in the above-described Equation (12). $2\phi((q_i - q_k)/2)$ in Equation (44) is actually calculated, and $\delta\phi$ is calculated by numerical integration.

Figure 5:
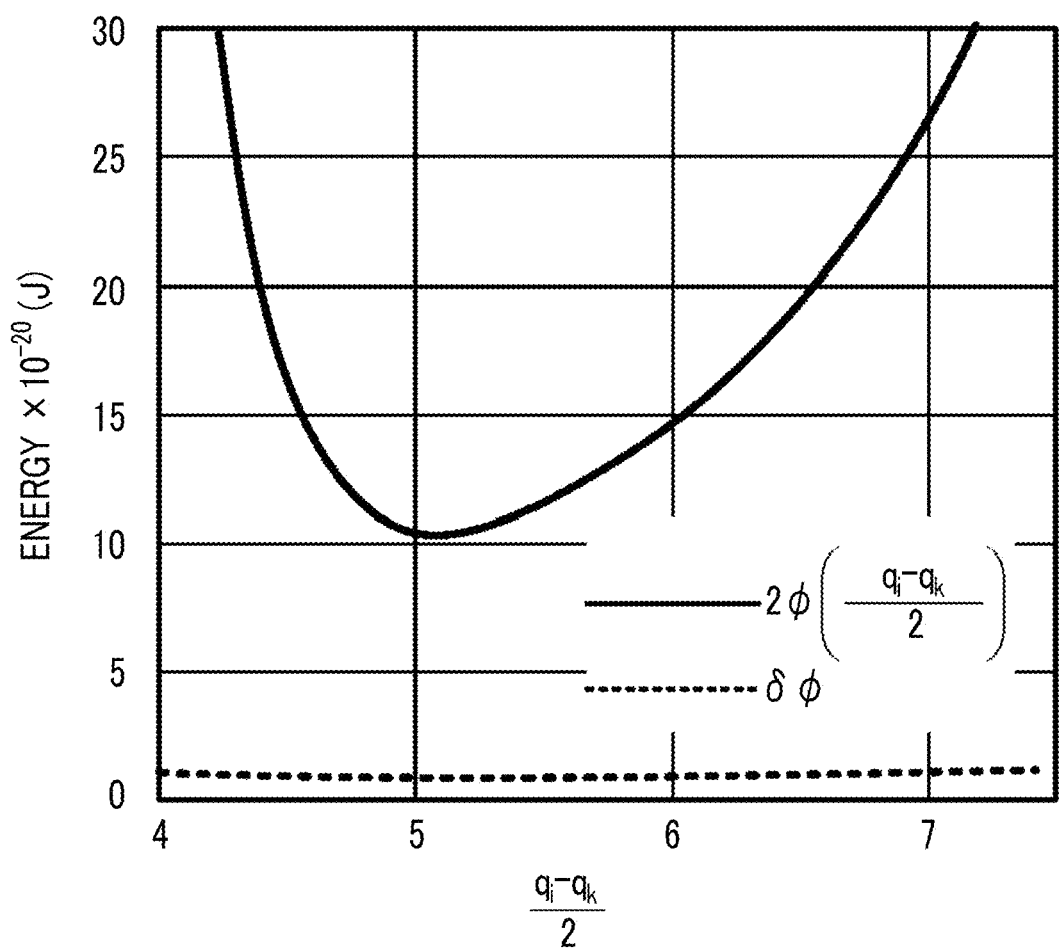
FIG. 5 is a graph showing a calculation result of $2\phi((q_i - q_k)/2)$ and a numerical integration result of δφ.

FIG. 5 shows a calculation result of $2\phi((q_i - q_k)/2)$ and a numerical integration result of $\delta\phi$. A transverse axis represents $(q_i - q_k)/2$, and a longitudinal axis represents energy in the unit of "J". A solid in FIG. 5 indicates the calculation result of $2\phi(q_i - q_k)/2)$, and a broken line indicates the numerical integration result of $\delta\phi$. It can be understood from the calculation results in FIG. 5 that a variation of $\delta\phi$ is sufficiently smaller than a variation of $2\phi(q_i - q_k)/2)$. Accordingly, $\delta\phi$ may be approximated as a constant with respect to $2\phi(q_i - q_k)/2)$.

From the above-described review, the following equation is derived.

$$\int_{q_k + r_a}^{q_k - r_a} dq_j \exp[-\beta\{\phi(q_i - q_j) + \phi(q_j - q_k)\}] \propto \exp\left[-2\beta\phi\left(\frac{q_i - q_k}{2}\right)\right] \quad (49)$$

This equation is equivalent to Equation (31) described in the coarse graining of the interaction potential $\phi = U_0$. Accordingly, coarse graining of an interaction potential $\phi = U_0 + U_{ch}$ may be handled in a similar way to the coarse graining of the interaction potential $\phi = U_0$.

Accordingly, the interaction potential $\phi'(r)$ in the normalized granular system S' is expressed as the following equation.

$$\phi'(r) = U_0'(r) + U_{ch}'(r:\varepsilon, \sigma) \quad (50)$$

$$U_0'(r) = \varepsilon' f\left(\frac{r}{\sigma'}\right)$$

$$U_{ch}'(r:\varepsilon, \sigma) = U_{ch}(r:\varepsilon', \sigma') = \varepsilon' f_{ch}\left(\frac{r}{\sigma'}\right)$$

In a case where the renormalization transformation law of Equation (13) is applied to the above-mentioned equation, the following equation is obtained.

$$\phi'(r) = \lambda^d \phi\left(\frac{r}{\lambda}\right) \quad (51)$$

In a case where a simulation is performed, Equation (51) may be applied thereto. In this case, by calculating a potential $\phi(r/\lambda)$ by replacing a variable r of the interaction potential $\phi(r)$ in the granular system S with $r/\lambda$, and multiplying the result by $\lambda^d$, it is possible to perform numerical value calculation with respect to the granular system S'.

[Renormalization Transformation Law in Consideration of the Number of Polymers and the Number of Monomer Grains in a Polymer]

Next, the renormalization transformation law in a case where the number of polymers is Np and the number of monomer grains in a polymer is Nm will be described with reference to FIG. 6.

Figure 6:
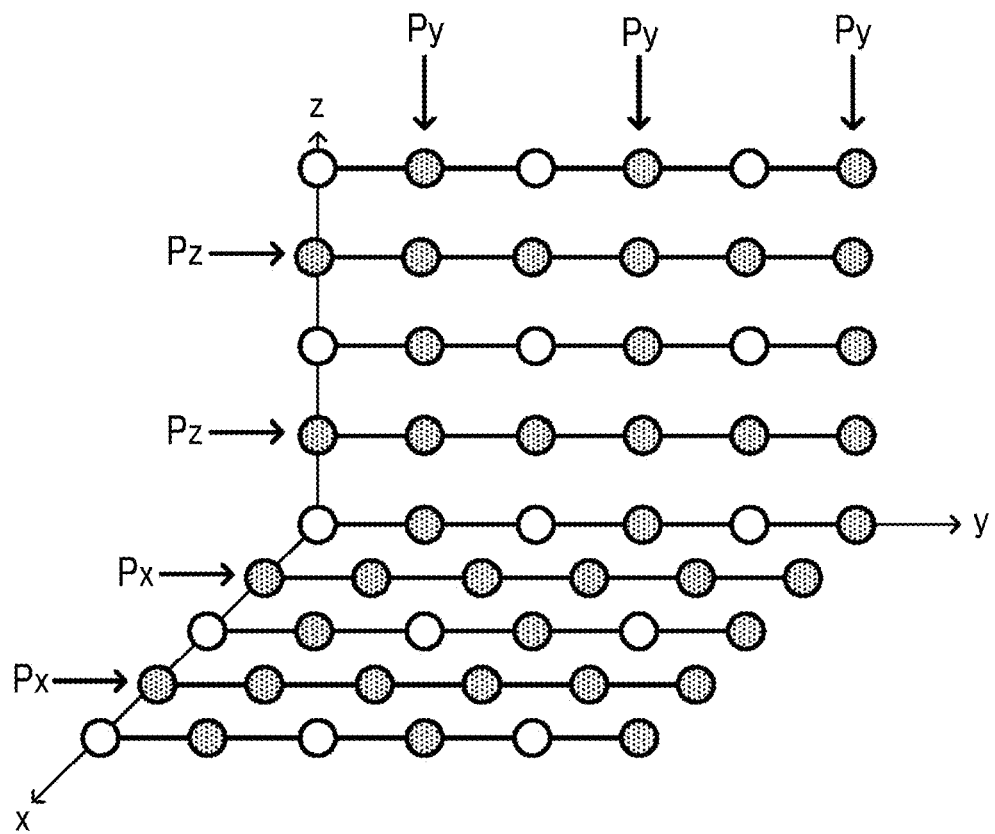
FIG. 6 is a schematic diagram showing an example in which linear polymers are regularly arranged in a 3-dimensional direction.

FIG. 6 is a schematic diagram showing a state where linear polymers are regularly arranged in three dimensions. Monomer grains that form each polymer are connected in the y direction. Plural polymers are arranged in the x, y, and z directions.

In a case where renormalization is performed once in the y direction, monomer grains that are arranged in the y direction are alternately eliminated. For example, monomer grains that are arranged on a face indicated by arrows Py are eliminated. Thus, the number of monomer grains in the polymer becomes ½ times. Then, in a case where renormalization is performed once in the x direction, polymers that are arranged in the x direction are alternately eliminated. For example, monomer grains that are arranged on a face indicated by arrows Px are eliminated. Thus, the number of polymers becomes ½ times. Then, in a case where renormalization is performed once in the z direction, polymer that are arranged in the z direction are alternately eliminated. For example, monomer grains that are arranged on a face indicated by arrows Pz are eliminated. Thus, the number of polymer also becomes ½ times.

As described above, in a case where renormalization is once performed in three-dimensional directions, the number of monomer grains becomes ½ times, and the number of polymers becomes ¼. When the number of times of renormalization is n, a renormalization transformation law in Nm and Np is obtained as shown in Equation (13).

Using the simulation method according to the above-described embodiment and a simulation method in which renormalization transformation is not performed, a strain rate dependency of a viscosity that is a specific phenomenon in a high molecular polymer is calculated. As a calculation method, an SLLOD method is used. Parameters of a simulation target are as follows.

m=42.3 g/mol $\varepsilon/k_B$=443.0 K $\sigma$=5.3×10$^{-10}$ m k=6.53×10$^{-1}$ N/m $R_0$=7.95×10$^{-10}$ m

T=443.0 K

Nm'=64

Np'=1000

Here, $k_B$ is a Boltzmann's constant. $\varepsilon$, $\sigma$, k, and $R_0$ are parameters that are shown in Equation (12) and Equation (45). The parameters k and $R_0$ are determined by $\varepsilon$ and $\sigma$ of the Lennard-Jones potential (Equation (12)). k' and $R_0$' in the granular system S' after renormalization are determined by $\varepsilon$' and $R_0$' after renormalization.

Figure 7:
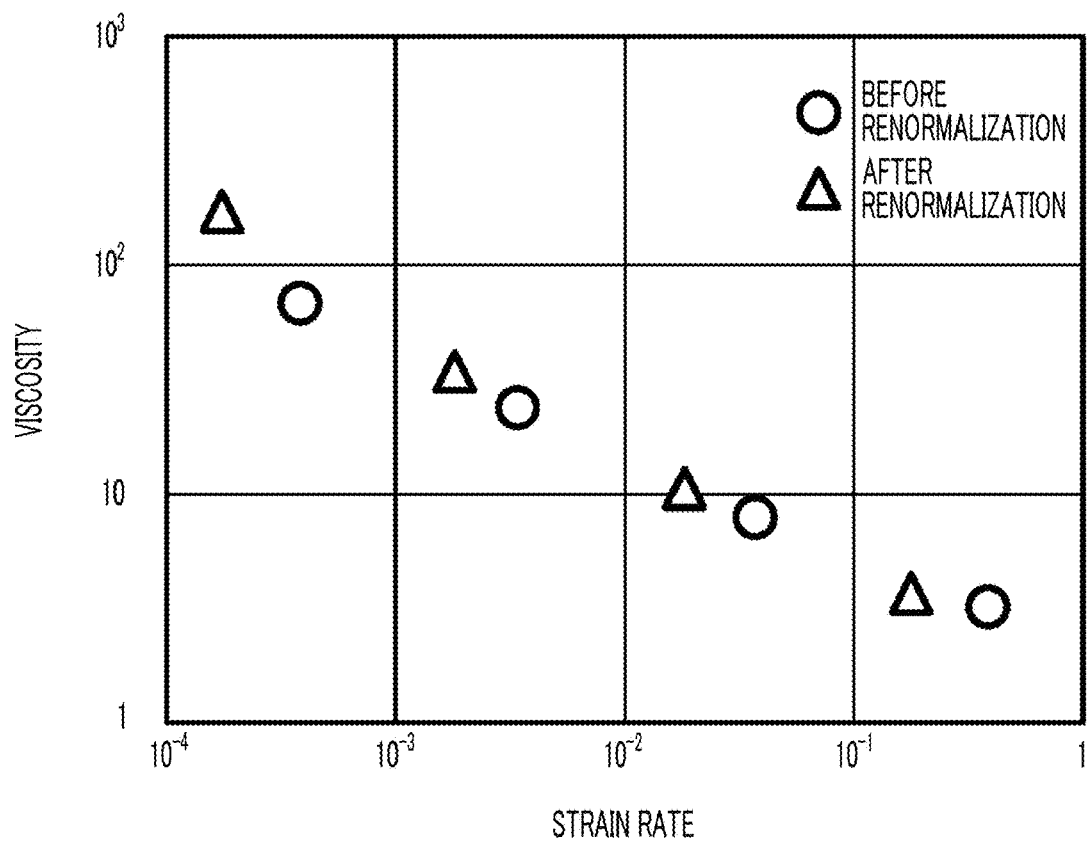
FIG. 7 is a graph showing a result obtained by simulating a strain rate dependency of a viscosity of a high molecular material.

FIG. 7 shows a simulation result. A transverse axis represents a strain rate, and a longitudinal axis represents a viscosity. In FIG. 7, the strain rate and the viscosity are expressed in no dimension. Circular signs in FIG. 7 indicate a result obtained by simulating the granular system S in which renormalization transformation is not performed, and triangular signs indicate a result obtained by simulating the granular system S' in which renormalization transformation is performed. It can be understood that viscosities calculated for the granular system S' after renormalization ride on a curve obtained by connecting viscosities calculated for the granular system S before renormalization. In this way, even in the granular system S' in which renormalization is performed, the strain rate dependency of the viscosity is maintained.

From the simulation result shown in FIG. 7, it is shown that it is possible to perform macroscopic calculation of high molecular polymer materials using the simulation method that uses the renormalization transformation law according to the above-described embodiment.

The simulation method according to the embodiment may be realized by causing a computer to execute a computer program. The computer program may be provided in a state of being recorded on a data recording medium, for example. Alternatively, the computer program may be provided through an electric communication line.

Figure 8:
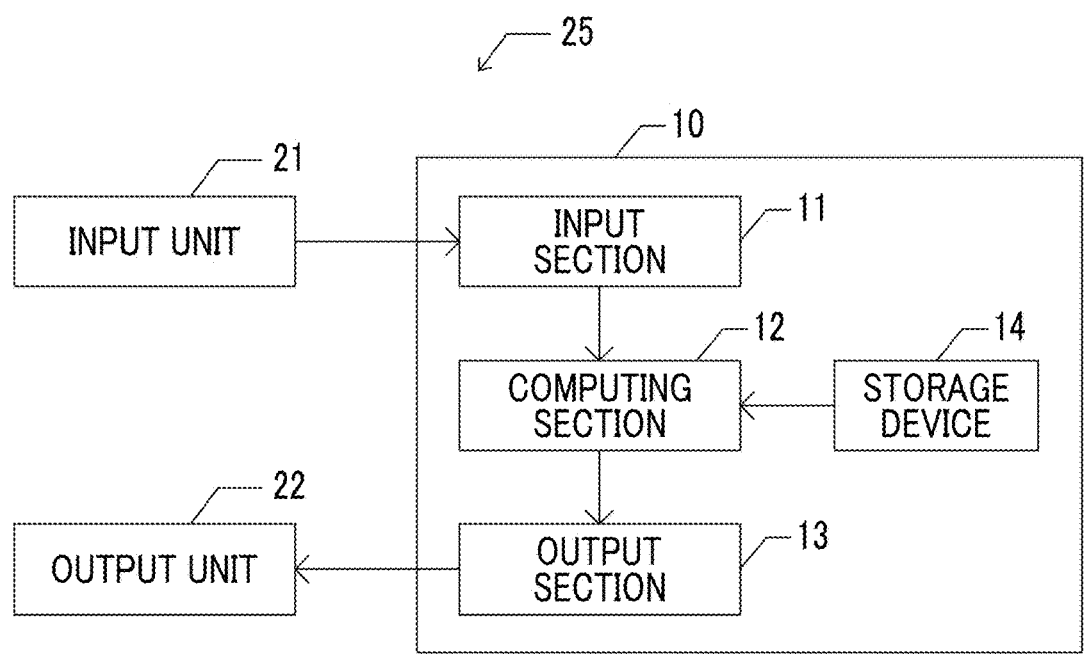
FIG. 8 is a block diagram of a simulation device according to an embodiment.

FIG. 8 is a block diagram of a simulation device 25 according to an embodiment. The simulation device 25 includes an input unit 21, a processing unit 10, and an output unit 22. The processing unit 10 includes an input section 11, a computing section 12, and an output section 13, and a storage device 14.

Various conditions of a simulation are input to the input section 11 through the input unit 21. For example, values of a dimensionality d of a space, a mass m of a monomer grain, the number of monomer grains $N_m$ that form one polymer, and the number of polymers Np, which are parameters that characterizes the granular system S which is a simulation target, and initial conditions of the granular system S, are input.

A computer program for executing the simulation is stored in the storage device 14. The computing section 12 executes the computer program stored in the storage device 14 on the basis of data input through the input section 11, to thereby execute a simulation process. A simulation result is output to the output unit 22 through the output section 13.

The computing section 12 performs the renormalization transformation process with respect to the parameters of the input granular system S, to thereby calculate parameters of the renormalized granular system S'. Molecular dynamics calculation with respect to the granular system S' is performed using the calculated parameters. Since the molecular dynamics calculation is performed with respect to the renormalized granular system S', it is possible to reduce a calculation time.

It should be understood that the invention is not limited to the above-described embodiment, but may be modified into various forms on the basis of the spirit of the invention. Additionally, the modifications are included in the scope of the invention.

What is claimed is:

1. A simulation method comprising:
   a process of performing a renormalization transformation process with respect to a granular system S that is a simulation target that includes a plurality of polymers that are respectively formed of a plurality of monomer grains that are connected to each other in one dimension, on the basis of a renormalization factor $\lambda$ depending on the number of times of renormalization; and
   a process of calculating a position vector and a momentum vector of a monomer grain in a renormalized granular system S' by executing molecular dynamics calculation with respect to the renormalized granular system S',
   wherein when a distance between monomers in the granular system S and the granular system S' is represented as r, a dimensionality of a space is represented as d, a mass of a monomer in the granular system S is represented as m, the number of monomer grains that form one polymer is represented as Nm, the number of polymers is represented as Np, and a coordinate of the monomer grain is represented as q,
   as an interaction potential $\phi(r)$ between the monomer grains, the following equation is applied in unspecified monomer grains, $$\phi(r) = U_0(r)$$

where a potential $U_0(r)$ is expressed as follows, using a parameter $\varepsilon$ having a dimension of energy, a parameter $\sigma$ having a dimension of a length, and a non-dimensional function f, $$U_0(r) = \varepsilon f\left(\frac{r}{\sigma}\right)$$

the following equation obtained by adding a finite extension non-linear elastic potential $U_{ch}(r: \varepsilon, \sigma)$ having the parameters $\varepsilon$ and $\sigma$ used in the potential $U_0(r)$ as parameters to the potential $U_0(r)$ is applied in the monomer grains that are adjacent to each other in the same polymer, $$\phi(r) = U_0(r) + U_{ch}(r:\varepsilon,\sigma)$$

when a mass of a monomer grain in the granular system S' is represented as m', the number of monomer grains that form one polymer is represented as Nm', the number of polymers is represented as Np', and a coordinate of the monomer grain is represented as q',
   the following transformation law is applied, and $$q' = q$$
   $$m' = m\lambda^d$$
   $$N'_m = \frac{N_m}{\lambda}$$
   $$N'_p = \frac{N_p}{\lambda^{d-1}}$$
   $$\varepsilon' = \varepsilon\lambda^d$$
   $$\sigma' = \sigma\lambda$$

the molecular dynamics calculation is executed with respect to the granular system S' using potentials $U_0'(r)$ and $U_{ch}'(r: \varepsilon, \sigma)$ in the granular system S' corresponding to the potentials $U_0(r)$ and $U_{ch}(r: \varepsilon, \sigma)$ in the granular system S expressed as follows:

$$U_0'(r) = \varepsilon' f\left(\frac{r}{\sigma'}\right)$$

$$U_{ch}'(\varepsilon, \sigma, r) = U_{ch}(r:\varepsilon', \sigma').$$

2. The simulation method according to claim 1, wherein the potential $U_0(r)$ in the granular system S is expressed as a form of a Lennard-Jones potential.

3. The simulation method according to claim 1, wherein the finite extension non-linear elastic potential $U_{ch}(r: \varepsilon, \sigma)$ is expressed as follows, using parameters k and $R_0$ depending on the parameters $\varepsilon$ and $\sigma$.

$$U_{ch}(r:\varepsilon, \sigma) = -\frac{1}{2}k \cdot R_0^2 \ln\left[1 - \left(\frac{r}{R_0}\right)^2\right] \quad (r \leq R_0)$$

$$U_{ch}(r:\varepsilon, \sigma) = \infty \quad (r > R_0).$$

4. A simulation device comprising:
an input unit through which values of a dimensionality d of a space, a mass m of a monomer grain, the number of monomer grains $N_m$ that form one polymer, and a value of the number of polymers Np, which are parameters that characterize a granular system S which is a simulation target that includes a plurality of polymers that are respectively formed of a plurality of monomer grains that are connected to each other in one dimension, and initial conditions of the granular system S, are input; and
a processing unit that executes a simulation process on the basis of data input through the input unit,
wherein the processing unit executes
a process of performing renormalization transformation on the basis of a renormalization factor $\lambda$ depending on the number of times of renormalization with respect to the granular system S, and
a process of calculating a position and a momentum of a monomer grain in a renormalized granular system S' by executing molecular dynamics calculation with respect to the renormalized granular system S',
wherein in the processing unit, when a distance between monomers in the granular system S and the granular system S' is represented as r and a coordinate of the monomer grain in the granular system S is represented as q,
as an interaction potential $\phi(r)$ between the monomer grains, the following equation is applied in unspecified monomer grains, $$\phi(r)=U_0(r)$$

where a potential $U_0(r)$ is expressed as follows, using a parameter $\varepsilon$ having a dimension of energy, a parameter $\sigma$ having a dimension of a length, and a non-dimensional function f, $$U_0(r) = \varepsilon f\left(\frac{r}{\sigma}\right)$$

the following equation obtained by adding a finite extension non-linear elastic potential $U_{ch}(r: \varepsilon, \sigma)$ having the parameters $\varepsilon$ and $\sigma$ used in the potential $U_0(r)$ as parameters to the potential $U_0(r)$ is applied in the monomer grains that are adjacent to each other in the same polymer, $$\phi(r)=U_0(r)+U_{ch}(r:\varepsilon,\sigma)$$

when a mass of a monomer grain in the granular system S' is represented as m', the number of monomer grains that form one polymer is represented as Nm', the number of polymers is represented as Np', and a coordinate of the monomer grain is represented as q',
the following transformation law is applied, and $$q' = q$$

$$m' = m\lambda^d$$

$$N_m' = \frac{N_m}{\lambda}$$

$$N_p' = \frac{N_p}{\lambda^{d-1}}$$

$$\varepsilon' = \varepsilon\lambda^d$$

$$\sigma' = \sigma\lambda$$

the molecular dynamics calculation is executed with respect to the granular system S' using potentials $U_0'(r)$ and $U_{ch}'(r: \varepsilon, \sigma)$ in the granular system S' corresponding to the potentials $U_0(r)$ and $U_{ch}(r: \varepsilon, \sigma)$ in the granular system S expressed as follows:

$$U_0'(r) = \varepsilon' f\left(\frac{r}{\sigma'}\right)$$

$$U_{ch}'(\varepsilon, \sigma, r) = U_{ch}(r:\varepsilon', \sigma').$$

5. A simulation method comprising:
a process of performing a renormalization transformation process with respect to a granular system S which is a simulation target that includes a plurality of polymers that are respectively formed of a plurality of monomer grains that are connected to each other in one dimension, on the basis of a renormalization factor $\lambda$ depending on the number of times of renormalization; and
a process of calculating a position vector and a momentum vector of a monomer grain in a renormalized granular system S' by executing molecular dynamics calculation with respect to the renormalized granular system S',
wherein when a distance between monomers in the granular system S and the granular system S' is represented as r, a dimensionality of a space is represented as d, a mass of a monomer in the granular system S is represented as m, the number of monomer grains that form one polymer is represented as Nm, the number of polymers is represented as Np, and a coordinate of the monomer grain is represented as q,
as an interaction potential $\phi(r)$ between the monomer grains, the following equation is applied in unspecified monomer grains, $$\phi(r)=U_0(r)$$

where a potential $U_0(r)$ is expressed as follows, using a parameter $\varepsilon$ having a dimension of energy, a parameter $\sigma$ having a dimension of a length, and a non-dimensional function f, $$\phi(r) = \varepsilon f\left(\frac{r}{\sigma}\right)$$

the following equation obtained by adding a finite extension non-linear elastic potential $U_{ch}(r: \varepsilon, \sigma)$ having the parameters $\varepsilon$ and $\sigma$ used in the potential $U_0(r)$ as parameters to the potential $U_0(r)$ is applied in the monomer grains that are adjacent to each other in the same polymer, $$\phi(r) = U_0(r) + U_{ch}(r)$$

when a mass of a monomer grain in the granular system S' is represented as m', the number of monomer grains that form one polymer is represented as Nm', the number of polymers is represented as Np', and a coordinate of the monomer grain is represented as q', the following transformation law is applied, and $$q' = q$$
$$m' = m\lambda^d$$
$$N'_m = \frac{N_m}{\lambda}$$
$$N'_p = \frac{N_p}{\lambda^{d-1}}$$

the molecular dynamics calculation is executed with respect to the granular system S' using a potential φ'(r) in the granular system S' corresponding to a potential φ(r) in the granular system S expressed as follows:

$$\phi'(r) = \lambda^d \phi\left(\frac{r}{\lambda}\right).$$

* * * * *